US010526261B2

(12) United States Patent
Wilson et al.

(10) Patent No.: US 10,526,261 B2
(45) Date of Patent: *Jan. 7, 2020

(54) METHODS OF MAKING CHLORINATED HYDROCARBONS

(71) Applicant: OCCIDENTAL CHEMICAL CORPORATION, Dallas, TX (US)

(72) Inventors: Richard L. Wilson, Mulvane, KS (US); Rodney L. Klausmeyer, Wichita, KS (US); John Lee Dawkins, Derby, KS (US); Daniel D. Rohrback, Valley Center, KS (US); James S. Strathe, LaPorte, TX (US); Lloyd B. Branam, Wichita, KS (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/980,932

(22) Filed: May 16, 2018

(65) Prior Publication Data
US 2018/0265438 A1 Sep. 20, 2018

Related U.S. Application Data

(60) Continuation of application No. 15/493,908, filed on Apr. 21, 2017, now Pat. No. 9,981,892, which is a
(Continued)

(51) Int. Cl.
C07C 17/25 (2006.01)
C07C 17/04 (2006.01)
(Continued)

(52) U.S. Cl.
CPC .............. *C07C 17/25* (2013.01); *C07C 17/04* (2013.01); *C07C 17/10* (2013.01); *C07C 17/275* (2013.01);
(Continued)

(58) Field of Classification Search
CPC ....... C07C 17/10; C07C 17/25; C07C 17/275; C07C 17/38; C07C 17/04; C07C 19/01; C07C 21/04; C07C 17/383; Y02P 20/127
See application file for complete search history.

(56) References Cited

U.S. PATENT DOCUMENTS 2,478,008 A  8/1949 Plump
3,823,195 A  7/1974 Smith
(Continued)

FOREIGN PATENT DOCUMENTS

EP  729932 A1  9/1996
JP  2000-086545 A  3/2000

OTHER PUBLICATIONS

Davis, et al. "Preparation of 1,1,1,3,3,3-Hexachloropropane" J. Am. Chem. Soc., vol. 73, No. 5, XP002518608, pp. 2361 (1951).
(Continued)

Primary Examiner — Jafar F Parsa
(74) Attorney, Agent, or Firm — Arthur M. Reginelli; Renner, Kenner

(57) ABSTRACT

Methods for the manufacture of 1,1,1,2,3-pentachloropropane from 1,1,1,3-tetrachloropropane and chlorine are disclosed. Improved methods are provided for the manufacture of 1,1,2,3-tetrachloropropene from 1,1,1,2,3-pentachloropropane. Methods are also disclosed for the manufacture of 1,1,2,3-tetrachloropropene from 1,1,1,3-tetrachloropropane and chlorine and for the manufacture of 1,1,2,3-tetrachloropropene from carbon tetrachloride, ethylene, and chlorine.

9 Claims, 6 Drawing Sheets

Related U.S. Application Data continuation of application No. 14/827,367, filed on Aug. 17, 2015, now Pat. No. 9,650,319, which is a continuation of application No. 14/554,883, filed on Nov. 26, 2014, now Pat. No. 9,139,495, which is a continuation of application No. 14/081,377, filed on Nov. 15, 2013, now Pat. No. 8,912,372, which is a continuation of application No. 13/588,240, filed on Aug. 17, 2012, now Pat. No. 8,614,363, which is a division of application No. 13/272,561, filed on Oct. 13, 2011, now Pat. No. 8,487,146, which is a division of application No. 12/337,409, filed on Dec. 17, 2008, now Pat. No. 8,115,038.

(60) Provisional application No. 61/014,981, filed on Dec. 19, 2007.

(51) Int. Cl.
| | | |
|---|---|---|
| *C07C 17/10* | (2006.01) | |
| *C07C 17/275* | (2006.01) | |
| *C07C 17/38* | (2006.01) | |
| *C07C 17/383* | (2006.01) | |
| *C07C 19/01* | (2006.01) | |
| *C07C 21/04* | (2006.01) | |

(52) U.S. Cl.
CPC ............ *C07C 17/38* (2013.01); *C07C 17/383* (2013.01); *C07C 19/01* (2013.01); *C07C 21/04* (2013.01); *Y02P 20/127* (2015.11)

(56) References Cited

U.S. PATENT DOCUMENTS

| | | |
|---|---|---|
| 4,000,312 A | 12/1976 | Piccardi |
| 4,535,194 A | 8/1985 | Woodard |
| 4,650,914 A | 3/1987 | Woodard |
| 5,902,914 A | 5/1999 | Rygas |
| 6,187,978 B1 | 2/2001 | Rygas |
| 6,193,221 B1 | 2/2001 | Sherman |
| 6,313,360 B1 | 11/2001 | Wilson |
| 7,094,936 B1 | 8/2006 | Owens |
| 7,102,041 B2 | 9/2006 | Tung |
| 8,115,038 B2 | 2/2012 | Wilson et al. |
| 8,722,946 B2 | 5/2014 | Close |
| 2004/0225166 A1 | 11/2004 | Wilson |
| 2008/0091053 A1 | 4/2008 | Tung |
| 2009/0032437 A1 | 2/2009 | Fong et al. |
| 2009/0216055 A1 | 8/2009 | Wilson |
| 2012/0035402 A1 | 2/2012 | Wilson et al. |

OTHER PUBLICATIONS

Henne, et al. "The preparation of Directed Chlorination of 1,1,1-Trifluoropropane" J. Am. Chem. Soc., vol. 64, No. 5, XP002518624, pp. 1157-1159 (1942).

"Ext chem printout D1", XP55006765, pp. 1, "D6" as cited by European Patent Office Examination Division in Communication dated Sep. 19, 2011 (1949).

Shakhnazaryan, et al. "Synthesis and Reactions of 4-Substituted Terahydro-5-0XO-2-Furoic Acids" J. Organic Chemistry of the USSR, Maik Nauka-Interperiodica, RU, vol. 4, XP00814275, pp. 1527-1532 (Jan. 1, 1968).

Demand for International Preliminary Examination and Response to Written Opinion for Intl. Appl. No. PCT/US2008/087246, pp. 1-16 (dated Sep. 14, 2009).

International Preliminary report on patentability for Intl. Appl. No. PCT/US2008/087246, pp. 1-15 (dated Mar. 17, 2010).

International Search Report and Written Opinion of the International Searching Authority issued in corresponding International Application No. PCT/US2008/087246, pp. 1-9 (dated Mar. 26, 2009).

English Translation of Office Action from the Patent Office of the State Intellectual Property Office of China dated Aug. 2, 2012 in the corresponding Appl. Serial No. 200880122115.0 in China.

English Translation of Office Action from the Patent Office of the State Intellectual Property Office of China dated May 20, 2013 in the corresponding Appl. Serial No. 200880122115.0 in China.

English Translation of the claims from the Patent Office of the State Intellectual Property Office of China in the corresponding Appl. Serial No. 200880122115.0 in China.

Figure 1: An inventive process to make 1,1,1,2,3-pentachloropropane
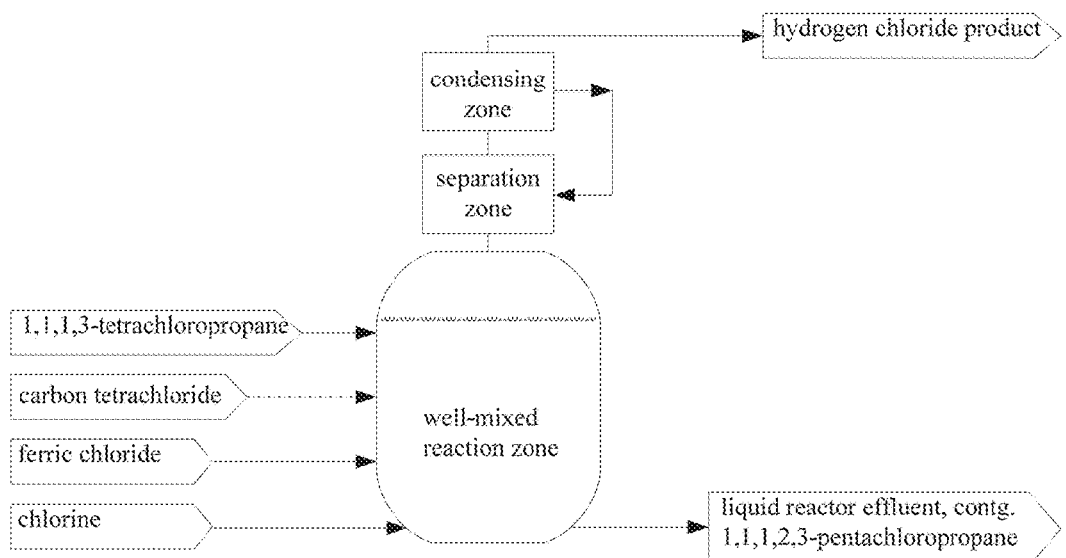

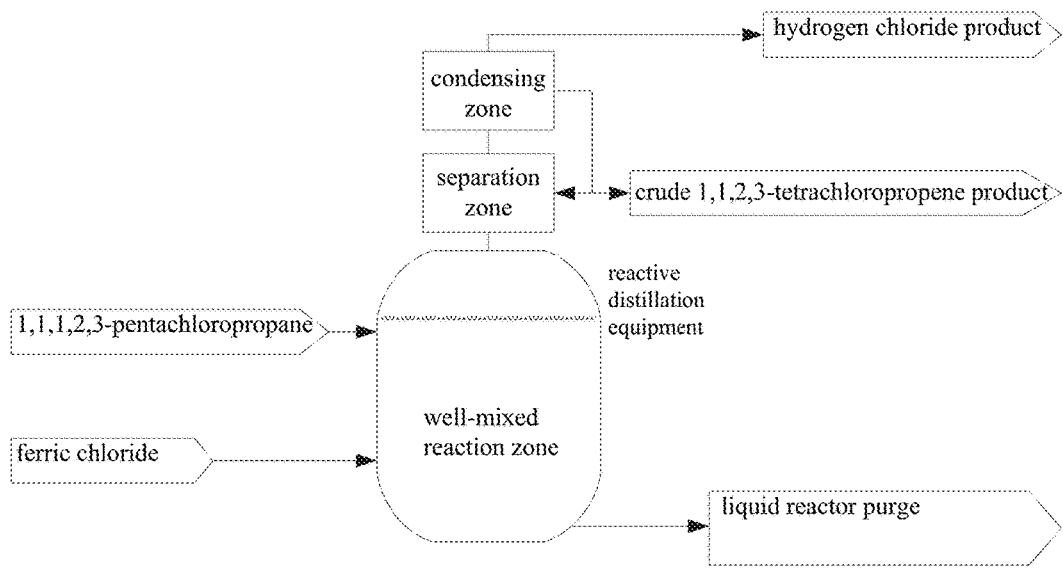
Figure 2: An inventive process to make 1,1,2,3-tetrachloropropene.

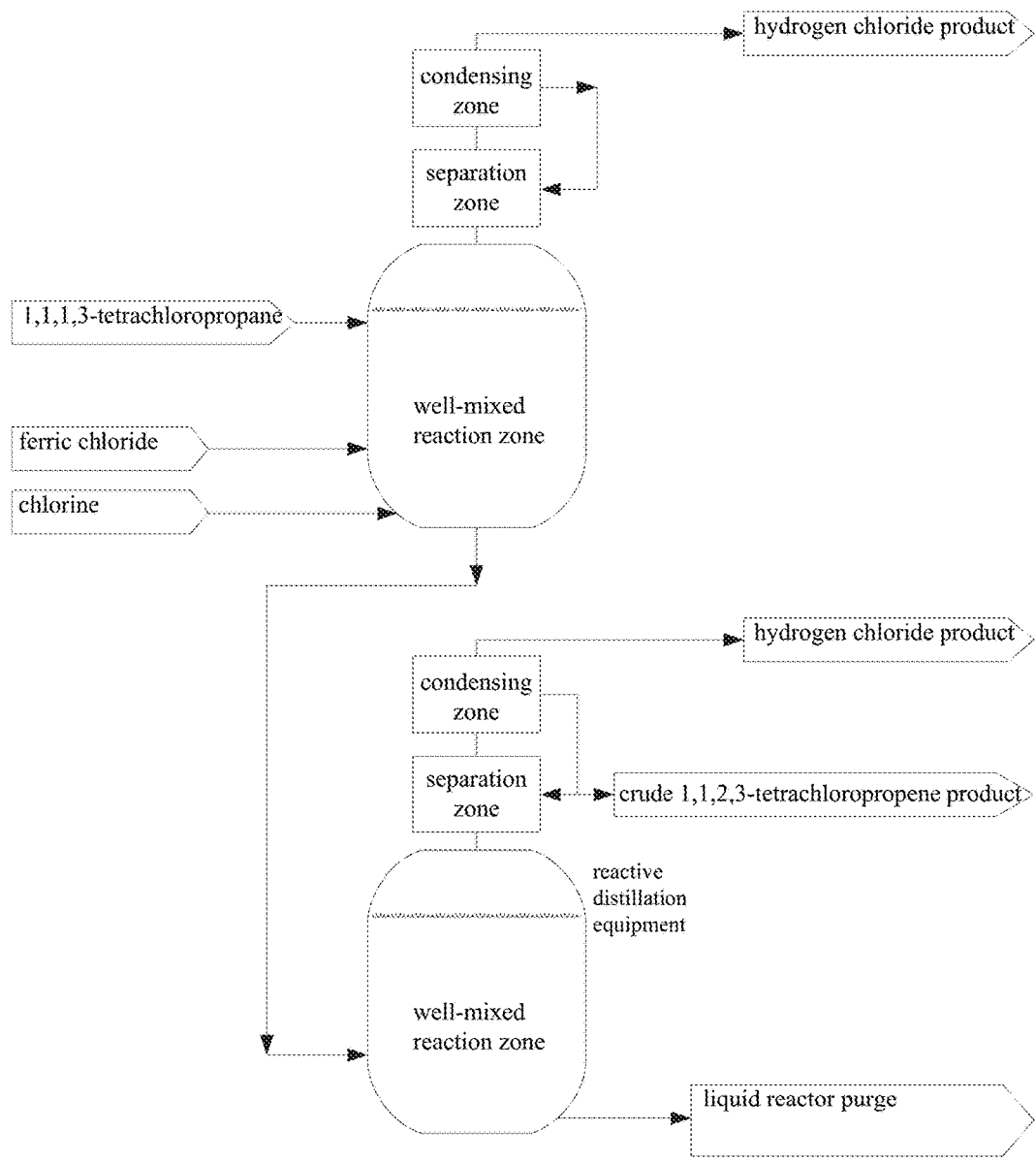
Figure 3: An inventive process to make 1,1,2,3-tetrachloropropene

Figure 4: An inventive process to make 1,1,2,3-tetrachloropropene
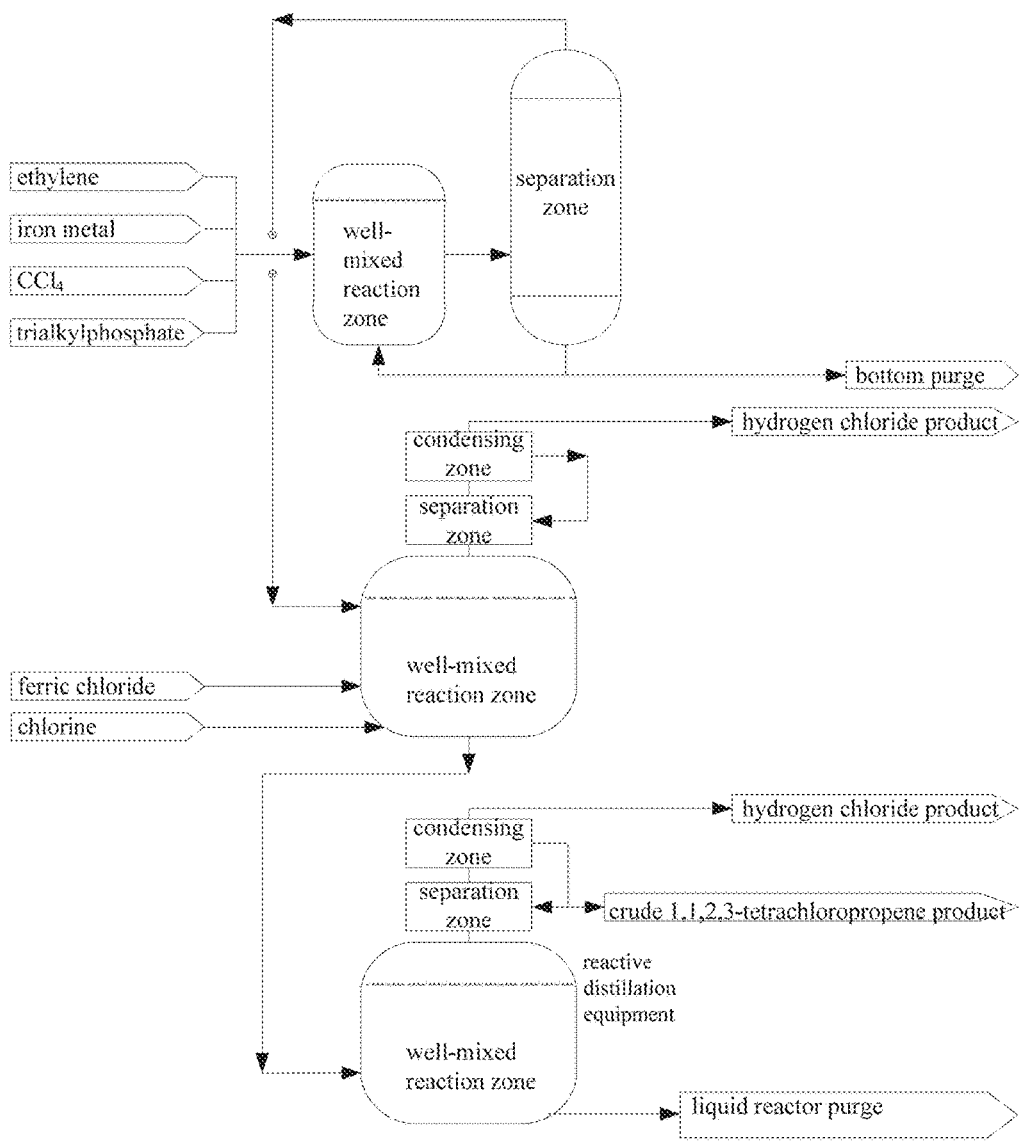

Figure 5: Results of Examples 2-4.
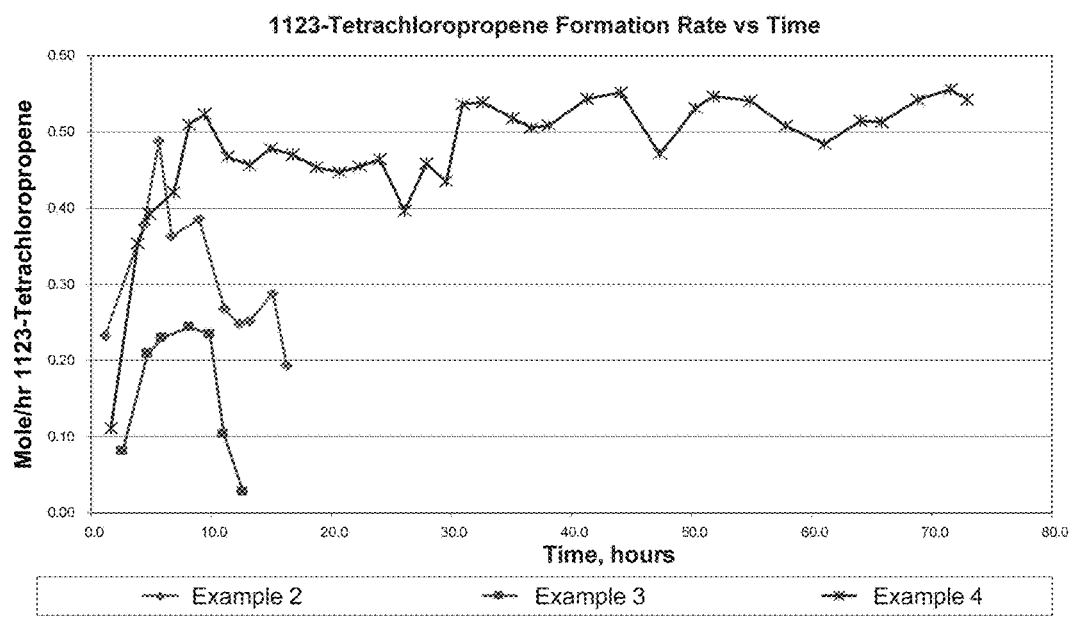

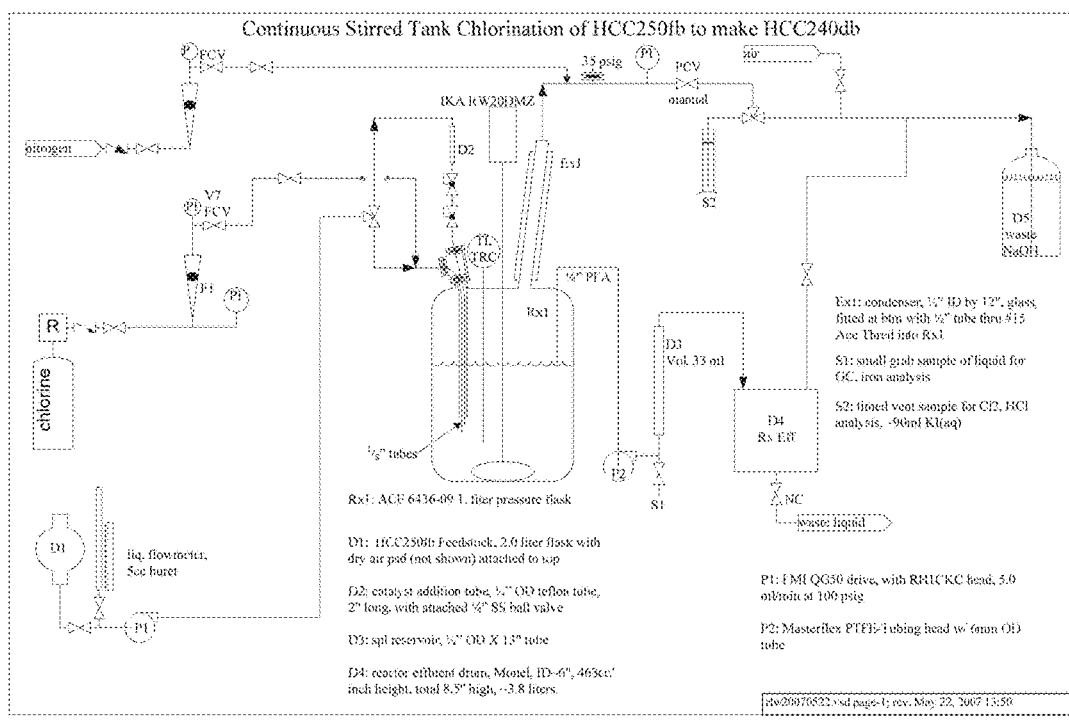
Figure 6: Lab Equipment for Continuous HCC240db Reaction

METHODS OF MAKING CHLORINATED HYDROCARBONS

CROSS-REFERENCE TO RELATED APPLICATIONS

This application is a continuation application of U.S. Non-Provisional application Ser. No. 15/493,908 filed on Apr. 21, 2017, which is a continuation application of U.S. Non-Provisional application Ser. No. 14/827,367 filed on Aug. 17, 2015 and issued as U.S. Pat. No. 9,650,319, which is a continuation application of U.S. Non-Provisional application Ser. No. 14/554,883 filed on Nov. 26, 2014 and issued as U.S. Pat. No. 9,139,495, which is a continuation application of U.S. Non-Provisional application Ser. No. 14/081,377 filed on Nov. 15, 2013 and issued as U.S. Pat. No. 8,912,372, which is a continuation application of U.S. Non-Provisional application Ser. No. 13/588,240 filed on Aug. 17, 2012 and issued as U.S. Pat. No. 8,614,363, which is a divisional application of U.S. Non-Provisional application Ser. No. 13/272,561 filed on Oct. 13, 2011 and issued as U.S. Pat. No. 8,487,146, which is a divisional application of U.S. Non-Provisional application Ser. No. 12/337,409 filed on Dec. 17, 2008 and issued as U.S. Pat. No. 8,115,038, and which claims the benefit of U.S. Provisional Application No. 61/014,981 filed on Dec. 19, 2007, the entire disclosure of each is hereby incorporated by reference in its entirety.

TECHNICAL FIELD

This invention relates to methods of manufacturing chloropropenes and chloropropanes, and more particularly to the manufacture of 1,1,2,3-tetrachloropropene and 1,1,1,2,3-pentachloropropane.

BACKGROUND

Chlorinated hydrocarbons are useful as feedstocks for the manufacture of refrigerants, polyurethane blowing agents, biocides, and polymers. 1,1,2,3-Tetrachloropropene, for example, is a commercially available product used as a feedstock for the herbicide Triallate (S-(2,3,3-trichloro-2-propenyl) bis(1-methylethyl)carbamothioate). 1,1,1,2,3-Pentachloropropane can be used as an intermediate for the manufacture of 1,1,2,3-tetrachloropropene. Methods for manufacturing 1,1,2,3-tetrachloropropene are described in the art, including in U.S. Pat. Nos. 4,535,194 and 4,650,914.

SUMMARY

The present application describes novel methods of making chlorinated hydrocarbons such as 1,1,2,3-tetrachloropropene and 1,1,1,2,3-pentachloropropane. These chlorinated hydrocarbons can be used, for example, as feedstocks to produce fluorocarbons. The 1,1,1,2,3-pentachloropropane may be used as an intermediate to produce 1,1,2,3-tetrachloropropene. The methods can provide for improved efficiency and provide for synergy in combinations of chemical reactions.

In one embodiment, the systems and methods disclosed herein include a process of making 1,1,1,2,3-pentachloropropane, the process comprising heating 1,1,1,3-tetrachloropropane in the presence of ferric chloride and chlorine to produce 1,1,1,2,3-pentachloropropane.

In another embodiment, the systems and methods disclosed herein include the manufacture of 1,1,2,3-tetrachloropropene, including dehydrochlorinating 1,1,1,2,3-pentachloropropane in a reaction zone in the presence of ferric chloride to produce 1,1,2,3-tetrachloropropene and hydrogen chloride, wherein the 1,1,2,3-tetrachloropropene and the hydrogen chloride are substantially continuously removed from the reaction zone as they form, via distillation.

In another embodiment, the systems and methods disclosed herein include a process for the manufacture of 1,1,2,3-tetrachloropropene, including (i) reacting 1,1,1,3-tetrachloropropane with chlorine in the presence of ferric chloride to produce crude 1,1,1,2,3-pentachloropropane; (ii) feeding crude 1,1,1,2,3-pentachloropropane into a reaction zone, to transform the crude 1,1,1,2,3-pentachloropropane into 1,1,2,3-tetrachloropropene and hydrogen chloride by dehydrochlorination, wherein the 1,1,2,3-tetrachloropropene and hydrogen chloride are removed from the reaction zone during the course of the dehydrochlorination reaction, the feeding and removal preferably being performed substantially continuously; and (iii) collecting 1,1,2,3-tetrachloropropene.

In another embodiment, the systems and methods disclosed herein include the manufacture of 1,1,2,3-tetrachloropropene, including (i) reacting carbon tetrachloride with ethylene in the presence of iron chlorides, iron metal, and a trialkylphosphate in a first reaction zone to produce reactor effluent containing 1,1,1,3-tetrachloropropane; (ii) distilling said reactor effluent to produce an overhead stream and a bottom stream, the overhead stream comprising a crude 1,1,1,3-tetrachloropropane solution comprising unreacted carbon tetrachloride and zero or more low-boiling contaminants, and the bottom stream comprising 1,1,1,3-tetrachloropropane, iron metal, iron compounds, one or more phosphorus-containing catalyst components, and high-boiling byproducts; (iii) reacting in a second reaction zone the overhead stream with chlorine in the presence of ferric chloride to produce crude liquid 1,1,1,2,3-pentachloropropane; (iv) feeding crude product from (iii) to a third reaction zone, which is part of a reactive distillation process, the reactive distillation process equipment comprising a reaction zone, a separation zone, and a condensing zone, to transform the crude 1,1,1,2,3-pentachloropropane into hydrogen chloride and 1,1,2,3-tetrachloropropene, wherein the hydrogen chloride and 1,1,2,3-tetrachloropropene are continuously removed from the reaction zone, and (v) recovering purified 1,1,2,3-tetrachloropropene product.

In another embodiment, the systems and methods disclosed herein include the manufacture of 1,1,2,3-tetrachloropropene, including: (i) reacting carbon tetrachloride with ethylene in the presence of iron chlorides, iron metal, and trialkylphosphate to produce a reactor effluent comprising 1,1,1,3-tetrachloropropane; (ii) distilling said reactor effluent to produce an overhead stream and a bottom stream, the overhead stream comprising a first crude 1,1,1,3-tetrachloropropane solution containing unreacted carbon tetrachloride and zero or more low-boiling contaminants, and the bottom stream comprising 1,1,1,3-tetrachloropropane, iron compounds, one or more phosphorus-containing catalyst components, and high-boiling byproducts; (iii) distilling the first crude 1,1,1,3-tetrachloropropane solution from ii) to produce a substantially pure carbon tetrachloride stream, comprising more than 90 weight percent (wt %) carbon tetrachloride, and a second crude 1,1,1,3-tetrachloropropane solution comprising no more than 10 wt % carbon tetrachloride; (iv) recycling a portion of the substantially pure carbon tetrachloride stream from (iii) to the reactor (i); (v) reacting the second crude 1,1,1,3-tetrachloropropane solution from iii) with chlorine in the presence of ferric chloride under conditions effective to produce a reactor effluent containing 1,1,1,2,3-pentachloropropane and ferric chloride; (vi) continuously feeding reactor effluent from (v) to a reactive distillation process, the reactive distillation process equipment comprising a reaction zone, a separation zone, and a condensing zone, to transform the crude 1,1,1,2,3-pentachloropropane into hydrogen chloride and 1,2,3-tetrachloropropene, wherein the hydrogen chloride and 1,1,2,3-tetrachloropropene are continuously removed from the reaction zone, and (vii) recovering 1,1,2,3-tetrachloropropene product.

One or more of the following features may be included in the embodiments:

the 1,1,1,3-tetrachloropropane, ferric chloride and chlorine may be heated in a liquid mixture with carbon tetrachloride;

the carbon tetrachloride may be present in an amount up to about 50 wt % of the reaction mixture, preferably in an amount from 3 to 30 wt % of the reaction mixture;

the ferric chloride may be present in a catalytic amount, such as in a range of from about 10 to about 1000 ppm, for example about 10 to about 1000 ppm or about 30 to about 1000 ppm or about 50 ppm to about 1000 ppm;

the reaction temperature may be from about 40° C. to about 120° C., and the reaction pressure may be in the range from about 1-300 psig;

the process may be a continuous process, and the 1,1,1,3-tetrachloropropane and chlorine may be continuously fed into a reaction zone containing ferric chloride; the ferric chloride may be continuously fed into a reaction zone, or periodically fed into a reaction zone; the 1,1,1,3-tetrachloropropane and chlorine may be introduced with a feed ratio of from about 0.9 to about 1.1 mole chlorine per mole tetrachloropropane;

the ferric chloride may be fed into a reaction zone at least once per 0.5 to 3 liquid turnovers (wherein one turnover is the time calculated as the ratio of liquid inventory in the reactor to the liquid flow rate out of the reactor);

addition of reagents and removal of products may be performed continuously, substantially continuously, or batch-wise periodically.

One or more of the following additional features may also be included in the embodiments:

at least a portion of the process may occur in equipment comprising a reaction zone, a separation zone, and a condensing zone; the separation zone may include a distillation component;

hydrogen chloride may be a coproduct of the process and may be removed from the reaction zone through a separation zone and a condensing zone; the hydrogen chloride coproduct exiting the reaction zone contains impurities, such as one or more of 1,1,3-trichloropropene or carbon tetrachloride; the carbon tetrachloride and/or 1,1,3-trichloropropene are recycled into the reaction zone via the condensing zone; the separation zone comprises an empty tube or a tube containing packing or other structure suitable for promoting vapor-liquid contacting, and the condensing zone comprises a vessel suitable for causing some of the components of the hydrogen chloride stream, such as 1,1,3-trichloropropene or carbon tetrachloride, to condense as a liquid; crude 1,1,1,2,3-pentachloropropane may be continuously removed from the reaction zone; 1,1,1,2,3-pentachloropropane may be dehydrochlorinated to produce 1,1,2,3-tetrachloropropene, and the crude 1,1,1,2,3-pentachloropropane reactor effluent may be dehydrochlorinated directly, without prior purification and without added catalysts or reagents; and the 1,1,2,3-tetrachloropropene product may be substantially free of 2,3,3,3-tetrachloropropene.

In some embodiments, the methods provide for fewer processing steps than was disclosed in the art. In some embodiments, the methods avoid the use of certain reagents that were disclosed in the art methods. In some embodiments, the methods reduce the waste streams produced relative to the art methods.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows a continuous process to produce 1,1,1,2,3-pentachloropropane from a feedstock containing 1,1,1,3-tetrachloropropane.

FIG. 2 shows a continuous process for the manufacture of 1,1,2,3-tetrachloropropene from a feedstock containing 1,1,1,2,3-pentachloropropane.

FIG. 3 shows a two-step continuous process to make 1,1,2,3-tetrachloropropene from feedstocks containing 1,1,1,3-tetrachloropropane and chlorine.

FIG. 4 shows a three-step continuous process to make 1,1,2,3-tetrachloropropene from ethylene, carbon tetrachloride, and chlorine feedstocks.

FIG. 5 is a graph depicting the rate of formation of 1,1,2,3-tetrachloropropene versus time, in connection with Examples 2-4.

FIG. 6 depicts the lab equipment used in an Exemplary continuous process to produce 1,1,1,2,3-pentachloropropane.

Like reference symbols in the various drawings indicate like elements.

DETAILED DESCRIPTION

1. Processes for Producing 1,1,1,3-Tetrachloropropane

In some embodiments, 1,1,1,3-tetrachloropropane is produced as described in one of US20040225166A1, US2003000648709, or US20040027520, the contents of each of which is hereby incorporated by reference.

US20040225166A1 describes a process for the synthesis of 1,1,1,3-tetrachloropropane in which a fraction of the catalyst and cocatalyst are separated after the reaction and recycled wherein the reaction mixture is distilled in a catalyst recovery unit resulting in the formation of "overhead fraction". This overhead fraction contains 1,1,1,3-tetrachloropropane and unreacted carbon tetrachloride, and some other components such as unreacted ethylene, or byproducts perchloroethylene, 1,2-dichloroethane, 1-chlorobutane, chloroform, or trichloropropene. The overhead fraction as described in US20040225166A1 can be further processed in methods and processes described herein, for example, conversion of the 1,1,1,3-tetrachloropropane into 1,1,1,2,3-pentachloropropane.

In some embodiments, the overhead fraction from the catalyst recovery unit as described in US20040225166A1 can be separated to produce both a stream containing an enhanced concentration of 1,1,1,3-tetrachloropropane and a stream containing an enhanced concentration of carbon tetrachloride. In this case, the recovered carbon tetrachloride and the relatively low-boiling byproducts contained therein can be partially recycled to a 1,1,1,3-tetrachloropropane reaction, for example, a reaction described in US20040225166A1. A small amount of the carbon tetrachloride can be purged from the system, for example, as waste, or as a feedstock for other processes. The purging of the carbon tetrachloride can be effected to control the concentration of low-boiling materials in the 1,1,1,3-tetrachloropropane reactor.

In some embodiments, the process producing 1,1,1,3-tetrachloropropane can produce a product that contains up to about 50 wt % carbon tetrachloride, for example, from about 3 to about 30 wt %, together with small amounts (e.g., less than about 5 wt % total) of materials such as perchloroethylene, 1,2-dichloroethane, 1-chlorobutane, chloroform, or trichloropropene. In general, the 1,1,1,3-tetrachloropropane product does not contain more than trace quantities (e.g., less than 1000 ppm each) of water or tributylphosphate or trialkylphosphate.

In some preferred embodiments 1,1,1,3-tetrachloropropane is produced by the reaction of carbon tetrachloride with ethylene in the presence of a catalyst as follows. Carbon tetrachloride ($CCl_4$) and ethylene are reacted in the presence of iron metal, iron chlorides, and a trialkyl phosphate, such as tributylphosphate (TBP), to produce 1,1,1,3-tetrachloropropane in a continuous or batch process. Excess carbon tetrachloride is fed into the reaction mixture, so that the product liquid contains unreacted carbon tetrachloride. The product liquid is distilled, producing an overhead mixture of carbon tetrachloride and 1,1,1,3-tetrachloropropane, and a bottoms mixture containing catalyst components (the iron and phosphorus containing species), 1,1,1,3-tetrachloropropane, and high-boiling byproducts.

In general, the term "batch process" refers to a mode of carrying out a chemical process in which the process begins with the reagents which are reacted under suitable reaction conditions for a suitable time and converted to product. The process is then terminated, and the reaction mixture containing the product is collected. The reaction mixture is typically further processed in order to isolate and/or purify the product from unreacted starting materials. On the other hand, the term "continuous process" refers to a mode of carrying out a chemical process in which, once the process has been established, reagents are added to a vessel in which reaction is occurring and products are simultaneously removed. Ideally, a continuous process may be operated to convert a substantially continuous stream of starting materials into a substantially continuous stream of products. "Substantially continuously" or "substantially continuous" when referring to addition of reagents, removal of products or other operations (such as heating, cooling, agitating, etc) performed as a part of chemical processes mean that the operation is carried out over a period of time during the course of the process, in contrast to batch-wise or periodic performance of such operations. The terms are not meant, however, to exclude the possibility of periodic interruption in the operation.

The bottoms mixture is generally partly recycled to the 1,1,1,3-tetrachloropropane reactor, and partly purged (e.g., in some instances, the purging can control catalyst degradation and high-boils concentration in the system). The term "high-boils" as used herein refers to materials that either are not volatile, or have normal boiling points higher than that of a preferred product, such as 1,1,1,3-tetrachloropropane. The normal boiling point of 1,1,1,3-tetrachloropropane is about 155 to 160° C. The overhead mixture of $CCl_4$ and 1,1,1,3-tetrachloropropane can be sent without further purification to a subsequent reaction step. Alternatively, some or most e.g., 0-100%, of the carbon tetrachloride can be separated e.g., from the 1,1,1,3-tetrachloropropane, and some or most of the carbon tetrachloride can be recycled to the 1,1,1,3-tetrachloropropane reactor, while the 1,1,1,3-tetrachloropropane is sent to the next reaction step. It is preferred that the mixture going to the next reaction step should contain from 3 to 30 wt % carbon tetrachloride, so that any excess over this amount may be separated and recycled or purged.

2. Processes for Producing 1,1,1,2,3-Pentachloropropane 1,1,1,2,3-Pentachloropropane may be formed by a process wherein 1,1,1,3-tetrachloropropane is reacted with chlorine in the presence of ferric chloride catalyst to produce 1,1,1,2,3-pentachloropropane and hydrogen chloride.

Without wishing to be bound by theory, it is believed that the 1,1,1,3-tetrachloropropane is dehydrochlorinated, in the presence of ferric chloride, producing 1,1,3-trichloropropene as an intermediate in situ, which adds chlorine in a reaction also catalyzed by ferric chloride, to produce 1,1,1,2,3-pentachloropropane as shown below. The present process, however, is generally carried out in one chemical operation, without the intermediate isolation or purification of 1,1,3-trichloropropene prior to the reaction which forms 1,1,1,2,3-pentachloropropane, although unreacted 1,1,3-trichloropropene may be collected and recycled into the process. Preferably the crude product from the process contains a ratio of at least 1.5:1 by weight of 1,1,1,2,3-pentachloropropane to 1,1,3-trichloropropene, more preferably at least about 2:1, 3:1, 5:1, 9:1, 10:1, 100:1, 1000:1, or 5000:1 or greater.

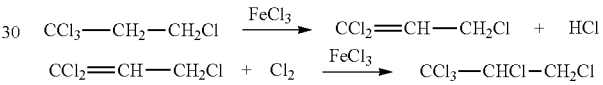

Further dehydrochlorination catalyzed by ferric chloride can result in formation of 1,1,2,3-tetrachloropropene as a desirable byproduct formed according to the following scheme:

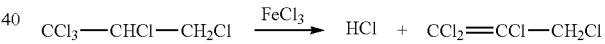

The 1,1,1,3-tetrachloropropane feedstock used as starting material for this process can generally be obtained by any convenient method. In some embodiments, the 1,1,1,3-tetrachloropropane feedstock may contain up to about 50 wt % carbon tetrachloride, and up to 5 wt % total of chlorinated hydrocarbons such as perchloroethylene, chloroform, 1,2-dichloroethane, chlorobutane, trichloropropene, etc. The 1,1,1,3-tetrachloropropane feedstock used generally does not contain more than 1000 ppm each of water, trialkylphosphate, alcohols, or other materials that strongly bind with or deactivate Lewis acid catalysts such as ferric chloride. The total amount of such deactivating compounds is preferably less than 1000 ppm by weight. The chlorine feedstock is generally substantially pure and dry; it contains less than about 0.5 wt % water, and more preferably less than 0.05 wt % water. The ferric chloride catalyst is generally anhydrous, containing no more than 3 wt % water. The ferric chloride catalyst is generally handled as a solid.

The reaction is generally performed by heating a reaction mixture containing 1,1,1,3-tetrachloropropane, ferric chloride and chlorine to produce 1,1,1,2,3-pentachloropropane. The reaction mixture may further contain carbon tetrachloride, for example in an amount up to about 50 wt % of the reaction mixture, for example from about 3 to about 30 wt %. The ferric chloride is preferably present in the mixture in a catalytic amount, preferably 25000 ppm or lower, for example about 5000 ppm, 2000 ppm, or 1000 ppm or lower. The ferric chloride may be present in an amount in the range of from about 10 to about 25000 ppm, from about 20 to about 5000 or about 20 to about 10000 ppm, from about 30 to about 2000 ppm, from about 30 to about 1000 ppm, or from about 50 to about 2000 ppm, or from about 50 to about 1000 ppm for example.

In some embodiments at least a portion of the process is performed in equipment which includes a reaction zone, a separation zone and a condensing zone.

Hydrogen chloride is a coproduct of the process. In some embodiments, the hydrogen chloride coproduct is removed from the reaction zone through a separation zone and a condensing zone. When the hydrogen chloride exits the reaction zone it may contain impurities, for example 1,1,3-trichloropropene and/or carbon tetrachloride. In some embodiments of the process, the separation zone may comprise an empty tube or a tube containing packing or other structure suitable for promoting vapor-liquid contacting, and the condensing zone may comprise a vessel suitable for causing some of the components of the hydrogen chloride stream, such as 1,1,3-trichloropropene or carbon tetrachloride, to condense as a liquid. In some embodiments of the process, the hydrogen chloride exiting the reaction zone contains 1,1,3-trichloropropene and/or carbon tetrachloride and 1,1,3-trichloropropene and/or carbon tetrachloride are recycled into the reaction zone via the condensing zone.

In some embodiments of the process, the reaction temperature for the reaction to form 1,1,1,2,3-pentachloropropane is in a range from about 40° C. to about 120° C.

In some embodiments of the process, the reaction pressure is in a range from about 1 to about 300 psig.

The 1,1,1,2,3-pentachloropropane can be produced in a semi-batch or continuous process.

For a semi-batch process, 1,1,1,3-tetrachloropropane liquid feedstock is generally placed with ferric chloride solid in a vessel equipped with means for agitation and temperature control. The mixture is generally heated and agitated at a temperature between 40° C. and 120° C., while chlorine gas is introduced below the surface of the liquid at a rate low enough that the reaction temperature remains controllable, and high enough to consume a substantial fraction of the 1,1,3-trichloropropene intermediate as it forms.

In a semi-batch operation, the various process conditions should be regulated so as to keep the 1,1,3-tetrachloropropene concentration in the liquid below about 20 wt % at all times during the reaction. In a continuous operation, the various process conditions should be regulated to keep the steady-state 1,1,3-tetrachloropropene concentration in the liquid below about 5 wt %.

The hydrogen chloride coproduct of the process forming 1,1,1,2,3-pentachloropropane is generally allowed to escape the reactor, for example, through a pressure control valve. The pressure is optionally controlled at from 0 to 300 psig, and more preferably from 2 to 100 psig. In some embodiments, the hydrogen chloride-containing stream is cooled to condense organic materials such as carbon tetrachloride or 1,1,3-trichloropropene, and return these materials to the reactor.

When the process is performed in semi-batch mode, it is not required to exactly match the rate of chlorine feed to the rate of 1,1,3-trichloropropene production, but in some preferred embodiments, the rates are set to substantially match. The rate of chlorine feed may be directly controlled. The rate of 1,1,3-trichloropropene production may be indirectly controlled, and may vary with time. The rate of 1,1,3-trichloropropene production may be influenced by the concentration of ferric chloride catalyst and the temperature. If too much chlorine is fed relative to the rate of 1,1,3-trichloropropene production, then unreacted chlorine can exit the reactor with hydrogen chloride coproduct. If too little chlorine is fed relative to the rate of 1,1,3-trichloropropene production, then a relatively high concentration of 1,1,3-trichloropropene can build up in the reactor. This material can be consumed by continued addition of chlorine. But high concentrations of 1,1,3-trichloropropene may be somewhat undesirable, as this condition can produce higher levels of high-boiling undesirable byproducts. In semi-batch mode, the rate of chlorine feed should preferably be controlled to limit the concentration of 1,1,3-trichloropropene in the reactor liquid to between about 0.03 and 20 wt % at any time during the reaction, and more preferably between 0.03 and 10 wt %.

Depending on the temperature and ferric chloride activity, and the chlorine feed rate, the semi-batch process can take, for example, from about 0.5 to about 24 hours to complete. Completion is generally marked by conversion of more than 90% of the 1,1,1,3-tetrachloropropane fed to products, and by conversion of more than 90% of the resulting 1,1,3-trichlororopropene to products.

For a continuous process, 1,1,1,3-tetrachloropropane liquid feedstock and chlorine gas are generally fed substantially continuously to a reactor equipped with means for agitation and temperature control. Hydrogen chloride coproduct is taken out continuously, optionally via a pressure control valve. In some embodiments, the hydrogen chloride-containing stream is cooled so that condensed organic materials such as 1,1,3-trichloropropene and carbon tetrachloride may be returned to the reactor. The liquid product can be taken out continuously, for example via such conventional means as a level-controlled pump, etc. In some preferred embodiments, the chlorine gas is sparged into the liquid.

Ferric chloride can be added substantially continuously or periodically. If the ferric chloride is added periodically, then a fixed amount is generally be added at least once per 0.5 to three turnovers of the reactor liquid, where turnover time is calculated as follows. The liquid reactor effluent flow rate is F [liters/hr], and the inventory of liquid in the reactor is V[liters]; which provide the turnover time as τ[hr]=V/F. Reactor liquid temperature is generally maintained between 40° C. and 120° C. Reactor pressure is generally maintained between 0 psig and 300 psig. Turnover time is generally between 0.5 hour and 24 hours. Ferric chloride concentration in the reactor liquid is generally in the range from about 30 ppm to about 1000 ppm, for example from about 30 ppm and about 1000 ppm, by weight. The chlorine/1,1,1,3-tetrachloropropane feed ratio is preferably about 0.90 to 1.10 mol/mol, and more preferably between 1.01 and 1.05 mol/mol.

Without wishing to be bound by any theory, it is believed that careful control of the chlorine/1,1,1,3-tetrachloropropane feed ratio is useful for at least two reasons. First, if too little chlorine is fed, then excessive amounts of compounds containing six carbon atoms can be formed. It may be that such six-carbon compounds form by the reaction of two three-carbon molecules, such as two 1,1,3-trichloropropene molecules. Second, if too much chlorine is fed, then excessive amounts of overchlorinated materials can be formed. Both of these circumstances could result in unwarranted consumption of valuable materials and production of unnecessary amounts of waste.

In some embodiments, the 1,1,1,3-tetrachloropropane feedstock contains from about 0.0 wt % to about 50 wt % carbon tetrachloride. It is preferable that the 1,1,1,3-tetrachloropropane feedstock should contain from 3 to 30 wt % carbon tetrachloride.

The reactor can be operated so as to produce very low concentrations of 1,1,3-trichloropropene in the effluent, for example, less than 3 wt %, or so as to produce considerable amounts, say, more than 3 wt %. If the intended application for the 1,1,3-trichloropropene is to make 1,1,1,2,3-pentachloropropane, then it is preferable to operate the reactor so as to produce very low concentrations of 1,1,3-trichloropropene in the liquid reactor effluent, and to return nearly all of the 1,1,3-trichloropropene contained in the hydrogen chloride vent stream to the reactor. If there are other desirable applications for 1,1,3-trichloropropene, then the reactor may be operated so as to produce both 1,1,3-trichloropropene, recoverable from the reactor vent stream, and 1,1,1,2,3-pentachloropropane, contained in the reactor liquid effluent stream. It is preferable in all cases to maintain low concentrations of 1,1,3-trichloropropene in the liquid reactor effluent.

The desired product produced by the processes described above is crude 1,1,1,2,3-pentachloropropane liquid. In some embodiments, the product also contains ferric chloride catalyst, and small amounts of one or more of unreacted 1,1,1,3-tetrachloropropane, 1,1,3-trichloropropene intermediate, 1,1,2,3-tetrachloropropene byproduct. In some embodiments, the crude product includes a small amount of undesired byproducts such as hexachloropropane. Optionally, the crude 1,1,1,2,3-pentachloropropane liquid further purified. The concentration of 1,1,1,2,3-pentachloropropane in the crude liquid is generally higher than 50 wt %. In some embodiments, the crude liquid contains up to about 30 wt % carbon tetrachloride. The concentration of 1,1,1,3-tetrachloropropane in the crude 1,1,1,2,3-pentachloropropane product is generally lower than about 5 wt %. In some embodiments of the process, crude 1,1,1,2,3-pentachloropropane is removed from the reaction zone. In some embodiments of the process, crude 1,1,1,2,3-pentachloropropane is removed from the reaction zone periodically. In some embodiments of the process, crude 1,1,1,2,3-pentachloropropane is removed from the reaction zone substantially continuously.

FIG. 1 depicts an exemplary process of making 1,1,1,2,3-pentachloropropane (HCC240db). As shown in FIG. 1, 1,1,1,3-tetrachloropropane, carbon tetrachloride, ferric chloride, and chlorine are fed into a reaction zone. The reaction is maintained at a temperature such that at least a portion of the reaction and products move into the separation and/or condensing zone. At least a portion of the hydrogen chloride product is removed by exiting the condensing zone. The 1,1,1,2,3-pentachloropropane product is removed from the reaction zone in a liquid effluent.

3. Processes for Producing 1,1,2,3-Tetrachloropropene 1,1,2,3-Tetrachloropropene may be formed by a process in which 1,1,1,2,3-pentachloropropane is dehydrochlorinated in the presence of ferric chloride catalyst to produce 1,1,2,3-tetrachloropropene product and hydrogen chloride coproduct.

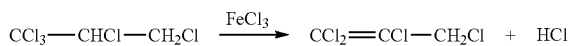

The 1,1,1,2,3-pentachloropropane used for the preparation of 1,1,2,3-tetrachloropropene may be prepared by one of the aforementioned processes for preparing 1,1,1,2,3-pentachloropropane. In some embodiments, the crude 1,1,1,2,3-pentachloropropane reactor effluent from a reactor in which 1,1,1,2,3-pentachloropropane is formed is dehydrochlorinated directly, without prior purification and without added catalysts or reagents.

In some embodiments, the 1,1,2,3-tetrachloropropene product is substantially free of 2,3,3,3-tetrachloropropene. The aforementioned ferric chloride-catalyzed dehydrochlorination may avoid the use of sodium hydroxide or aqueous alkali for dehydrochlorination of 1,1,1,2,3-pentachloropropane.

Purified 1,1,1,2,3-pentachloropropane or crude 1,1,1,2,3-pentachloropropane that contains ferric chloride catalyst is generally fed to a reactive distillation system. Alternatively, or in addition, ferric chloride may be separately added to the system. This would certainly be necessary if purified 1,1,1,2,3-pentachloropropane is employed as feedstock.

Ferric chloride may be added during the course of the reaction and such addition can be continuous or periodic. When ferric chloride is added, the ferric chloride may be added to the process periodically. For example, ferric chloride may be fed into the reaction zone at least once per 0.5 to 3 liquid turnovers, and wherein one turnover is the time calculated as the ratio of liquid inventory in the reactor to the liquid flow rate out of the reactor. Alternatively, the ferric chloride may be added continuously. The amount of ferric chloride maintained in the reaction zone is preferably a catalytic amount, for example about 50000 ppm or lower. The ferric chloride may be present in an amount in the range of from about 10 to about 50000 ppm, from about 100 to about 25000 ppm, or from about 1000 to about 20000 ppm, for example. In some embodiments, during the course of the reaction an amount in the range from about 30 to about 20000 ppm by weight, for example about 1000 to about 20000 ppm, of ferric chloride is maintained in the reaction zone.

A process for the preparation of 1,1,2,3-tetrachloropropene may use reactive distillation. In general such a process includes dehydrochlorinating 1,1,1,2,3-pentachloropropane in a reaction zone in the presence of ferric chloride to produce 1,1,2,3-tetrachloropropene and hydrogen chloride, wherein the 1,1,2,3-tetrachloropropene and the hydrogen chloride are removed from the reaction zone by distillation during the course of the dehydrochlorination reaction, for example being removed as they form, continuously or substantially continuously. Preferably, unpurified product liquid from the 1,1,1,2,3-pentachloropropane reactor, which already contains ferric chloride catalyst, is fed continuously to a reactive distillation system. The system can be equipped with a reaction zone, a separation zone, and a condensing zone. The feed enters the reaction zone, which is generally located below the separation zone. The liquid in the reaction zone is heated and agitated. Any means for providing agitation and heat can be used. For example, the agitation can be provided via pumped circulation loops, or by stirring. Heat can be provided through a jacket on the vessel, or by internal heat exchangers, or by external heat exchangers. Preferably, the reactor liquid does not contain more than 1000 ppm each of water, trialkylphosphate, alcohols, or other materials that strongly bind with or deactivate Lewis acid catalysts such as ferric chloride. The total of such deactivating compounds is generally less than 1000 ppm by weight. Optionally, means for adding more ferric chloride catalyst are included. Such addition can be continuous or periodic.

The reactive distillation system may be operated in a continuous process wherein reagent addition and product removal are performed at the same time.

When the process is performed as a continuous process, a reagent solution comprising 1,1,1,2,3-pentachloropropane and ferric chloride may be introduced periodically or substantially continuously into the reaction zone. The reagent solution may be a crude, partially purified or purified product from the above-described processes of preparing 1,1,1,2,3-pentachloropropane. The reagent solution used for the synthesis of 1,1,2,3-tetrachloropropene may further contain one or more of carbon tetrachloride, 1,1,3-trichloropropene, 1,1,1,3-tetrachloropropane, or hexachloropropane. The reaction zone may be substantially free of sodium hydroxide or aqueous sodium hydroxide.

In the reactive distillation system, products may be removed from the liquid reaction mixture reaction zone as well as by distillation.

In some embodiments, the liquid reaction mixture, which comprises unreacted 1,1,1,2,3-pentachloropropane, ferric chloride, non-volatile material, and high-boiling by-products, is removed from the reaction zone. The liquid reaction mixture may be removed continuously or substantially continuously from the reaction zone. Alternatively, the liquid reaction mixture may be removed periodically. The unreacted 1,1,1,2,3-pentachloropropane contained in the liquid reaction mixture removed from the reaction zone may be substantially separated from other components and recycled into the reaction zone.

Generally, two product streams exit the reactive distillation system. The bottom stream continuously or periodically removes high-boiling or non-boiling materials such as unreacted 1,1,1,2,3-pentachloropropane, hexachloropropane, pentachlorohexene, hexachlorohexane, and ferric chloride. The overhead stream continuously removes 1,1,2,3-tetrachloropropene product, hydrogen chloride, and, in some embodiments, unreacted 1,1,1,2,3-pentachloropropane, 1,1,3-tetrachloropropane, and 1,1,3-trichloropropene. The overhead stream generally removes carbon tetrachloride, if such is present in the feed.

The reactive distillation is generally performed using reactive distillation equipment which includes a reaction zone, a separation zone, and a condensing zone. The separation zone is generally positioned vertically above the reaction zone. In a simple embodiment, the separation could comprise a tube. In some embodiments, however, the separation zone may contain a surface, for example packing material or other structures, suitable for promoting efficient contact of vapor and liquid streams. The separation zone therefore promotes separation of more volatile and less volatile components of the reaction mixture.

The liquid in the reaction zone contains the ferric chloride catalyst, most of the unreacted pentachloropropane, and some of the reaction products. The dehydrochlorination reaction generally occurs in the reaction zone. The separation zone is generally operated at an overhead pressure of about 100 to about 600 torr, to provide a bottoms temperature in the reaction zone ranging from about 120° C. to about 180° C. The 1,1,2,3-tetrachloropropene product continuously exits the reaction zone through the separation zone, together with hydrogen chloride. In some embodiments, the separation zone keeps most of the unreacted 1,1,1,2,3-pentachloropropane in the reaction zone, and allows most of the 1,1,2,3-tetrachloropropene product to escape the reaction zone.

In the condensing zone, the vapor stream is generally cooled, thus causing 1,1,2,3-tetrachloropropene, unreacted 1,1,1,2,3-pentachloropropane, and components such as carbon tetrachloride, 1,1,1,3-tetrachloropropane, and 1,1,3-trichloropropane to condense. The uncondensed hydrogen chloride can be further purified or sent elsewhere for disposal or employment. In some embodiments, a portion of the condensate may be returned to the separation zone as reflux liquid, and a portion may be removed as product. For example, about 10% of the condensed 1,1,2,3-tetrachloropropene may be removed as product. The product may optionally be sent to a product purification system for further purification.

In some embodiments, a product purification system produces purified 1,1,2,3-tetrachloropropene product suitable for its intended application, and separates other components of the reactive distillation column overhead stream. For example, carbon tetrachloride, 1,1,3-trichloropropene, and/or 1,1,1,3-tetrachloropropane can be recovered in suitably pure form, and either recycled into any of the aforementioned chemical processes employing the particular compound, or else sent to other employment.

By operating the reactive distillation system at subatmospheric pressure, and thereby reduced temperature, tar and polymer formation can be reduced. A continuous or periodic purge can be taken from the reaction zone to maintain the ferric chloride concentration in a range from about 1000 ppm to about 20000 ppm by weight. This purge can also remove the catalytically inactive iron-containing tars and polymers, as well as catalyst poisons, if any are present. The purge thus can be operated to maintain catalytic activity and to remove high-boiling and non-boiling contaminants from the system.

Crude 1,1,2,3-tetrachloropropene product is generally continuously removed from the separation zone overhead. The continuous removal can reduce the quantity of 1,1,2,3-tetrachloropropene in contact with the ferric chloride catalyst in the reaction zone. While not being bound by theory, it is believed this reduces the likelihood of the olefin reducing the catalytically active ferric chloride to inactive ferrous chloride, which can help preserve the catalyst life. The crude 1,1,2,3-tetrachloropropene overhead product can be further distilled in a conventional manner to remove any undesired lower and higher boiling compounds.

FIG. 2 depicts an exemplary process for producing 1,1,2,3-tetrachloropropene. 1,1,1,2,3-Pentachloropropane and ferric chloride are fed into a reaction zone. The reaction zone is maintained at a temperature and pressure such that at least a portion of the reaction products move into the separation and/or condensing zones. At least a portion of the hydrogen chloride product is removed by exiting the condensing zone. At least a portion of crude 1,1,2,3-tetrachloropropene product is condensed in the condensing zone and subsequently removed from the process.

FIG. 3 depicts a synergistic process for producing 1,1,2,3-tetrachloropropene. 1,1,1,3-Tetrachloropropane, ferric chloride, and chlorine, and optionally carbon tetrachloride (not shown), are fed into a reaction zone shown in the upper portion of FIG. 3. The reaction is maintained at a temperature such that at least a portion of the reaction products move into the separation and/or condensing zones. At least a portion of the hydrogen chloride product is removed by exiting the condensing zone. The 1,1,1,2,3-pentachloropropane product is removed from the reaction zone in a liquid effluent and subsequently introduced into a second reaction zone shown in the lower portion of FIG. 3. The second reaction zone is maintained at a temperature such that at least a portion of the reaction products move into the separation and/or condensing zone. At least a portion of the hydrogen chloride product is removed by exiting the condensing zone. At least a portion of crude 1,1,2,3-tetrachloropropene product is condensed in the condensing zone and subsequently removed from the process.

FIG. 4 depicts an exemplary synergistic process for producing 1,1,2,3-tetrachloropropene. Ethylene, iron metal, carbon tetrachloride, and trialkylphosphate are introduced into a first reaction zone, shown near the top of FIG. 4. The liquid reactor effluent passes into a first separation zone, which separates the first reactor effluent into an overhead and a bottoms stream. The bottoms stream, which contains catalyst components, is partly returned to the first reaction zone and partly purged. The overhead stream, which contains 1,1,1,3-tetrachloropropane product and unreacted carbon tetrachloride, passes to a second reaction zone, shown near the center of FIG. 4. Chlorine and ferric chloride catalyst are also introduced into the second reaction zone, where 1,1,1,2,3-pentachloropropane and hydrogen chloride are produced. At least some of the hydrogen chloride product is removed as a gas via the overhead separation and condensing zones. At least some of the 1,1,3-trichloropropene byproduct and the carbon tetrachloride solvent, and other volatile organic materials, are condensed and returned to the reaction zone via the separation and condensing zones. The liquid effluent from the second reaction zone contains, at least, 1,1,1,2,3-pentachloropropane product and ferric chloride catalyst. This material is transferred to a third reaction zone, shown near the bottom of FIG. 4. In the third reaction zone, 1,1,1,2,3-pentachloropropane is catalytically dehydrochlorinated to produce 1,1,2,3-tetrachloropropene and hydrogen chloride. At least some of the 1,1,2,3-tetrachloropropene and hydrogen chloride products pass through the separation zone into the condensing zone, wherein some of the 1,1,2,3-tetrachloropropene is condensed, and thereby separated from hydrogen chloride gas. This partly purified hydrogen chloride gas is removed from the condensing zone. The condensed 1,1,2,3-tetrachloropropene product is partly returned to the separation zone as reflux liquid, and partly removed as crude 1,1,2,3-tetrachloropropene product liquid. The latter may be further purified by any known means. A liquid purge stream is taken from the third reaction zone. This stream contains ferric chloride catalyst, unreacted 1,1,1,2,3-pentachloropropane, and high-boiling or non-volatile byproducts.

EXAMPLES

Examples 1-4. Formation of 1,1,2,3-tetrachloropropene

The equipment used in examples 1-4 was a 20-tray, 25 mm i.d. vacuum-jacketed Pyrex laboratory distillation column equipped with a 1-liter bottoms flask and means for operation at sub-atmospheric pressure. A pump continuously fed liquid material directly into the bottoms flask. A swinging-bucket type reflux head allowed controlled withdrawal of overhead product. A separate pump removed liquid from the bottoms flask periodically.

Table 1 shows the run conditions for examples 1-4. Overhead formation rate of the 1,1,2,3-tetrachloropropene product is shown in FIG. 1.

TABLE 1

Conditions for Examples 1-4

| | | Example number | | | |
|---|---|---|---|---|---|
| | | 1 | 2 | 3 | 4 |
| overhead pressure | torr | 280 | 495 | 480 | 350 |
| bottoms temperature | ° C. | 159-160 | 173-177 | 169-179 | 154-157 |
| bottoms residence time | hr | 4.5 | 7 | 8 | 8 |
| liquid feed source | | Synthetic | Synthetic | tetrachloropropane chlorination | tetrachloropropane chlorination |
| liquid feed composition | | | | | |
| 1,1,1,2,3-pentachloropropane | wt % | 45.0 | 90.8 | 61.0 | 80.0 |
| misc. chlorocarbons | wt % | 55.0 | 9.2 | 39.0 | 20.0 |
| $FeCl_3$ | ppmw | 0 | 0 | 0 | 280 |
| solid $FeCl_3$ added | g | 0.27 | 0.96 | 0 | 0 |
| reactor $FeCl_3$ concentration | ppmw | 1000 | 2030 | 148 | 2100 | ppmw = parts per million by weight

Example 1

The bottoms flask of the distillation column was charged with a mixture of about 90 percent 1,1,1,2,3-pentachloropropane, with about 10 percent other miscellaneous chlorocarbons. About 0.27 grams of solid anhydrous ferric chloride was added to the liquid, with stirring, giving a bottoms ferric chloride concentration of 1000 ppmw. The column pressure was adjusted to 280 torr, and sufficient heat was applied to the bottoms flask to reflux liquid in the column. A synthetic feed comprised of 45 percent 1,1,1,2,3-pentachloropropane and 55 percent other miscellaneous chlorocarbons was fed continuously to the bottoms flask to give a liquid residence time in the bottoms of approximately 4.5 hours. The synthetic feed contained no ferric chloride. Liquid draw from the reflux head was started simultaneously with the feed at a rate sufficient to maintain the liquid level in the bottoms flask. The formation rate of 1,1,2,3-tetrachloropropene, as measured by the overhead liquid composition and collection rate, was less than 0.02 mole/hr, indicating very little dehydrochlorination of the pentachloropropane occurred. The bottoms temperature over the course of the test ranged from 159-160° C.

Example 2

The bottoms flask of a distillation column was charged with a mixture of about 96 percent 1,1,1,2,3-pentachloropropane, with about four percent other miscellaneous chlorocarbons. About 0.96 grams of solid anhydrous ferric chloride was added to the liquid, with stirring, to give a bottoms ferric chloride concentration of 2030 ppmw. The column pressure was adjusted to 495 torr, and sufficient heat was applied to the bottoms flask to reflux liquid in the column. A synthetic feed comprised of 90.8 percent 1,1,1,2,3-pentachloropropane and 9.2 percent other miscellaneous chlorocarbons was fed continuously to the bottoms flask so as to give a liquid residence time in the bottoms of approximately 7 hours. The feed contained no ferric chloride. Liquid draw from the reflux head was started simultaneously with the feed at a rate sufficient to maintain the liquid level in the bottoms flask. The formation rate of 1,1,2,3-tetrachloropropene, as measured by the overhead liquid composition and collection rate, peaked at 0.49 mole/hr, at 5.7 hours run time, as shown in FIG. 5. The formation rate then began to steadily fall to below 0.19 mole/hr at 16 hours. The bottoms temperature over the course of the test steadily increased from 173-177° C.

Example 3

A feed mixture containing 1,1,1,2,3-pentachloropropane was prepared by liquid-phase chlorination of 1,1,1,3-tetrachloropropane in the presence of dissolved ferric chloride. The unpurified chlorination product, containing approximately 80 percent 1,1,1,2,3-pentachloropropane, 20 percent other miscellaneous chlorocarbons, and 150 ppmw ferric chloride, was charged to the bottoms flask of the distillation column. No additional solid ferric chloride was added to the liquid. The column pressure was adjusted to 480 torr, and sufficient heat was applied to the bottoms flask to reflux liquid in the column. Then, a synthetic feed comprised of 61 percent 1,1,1,2,3-pentachloropropane and 39 percent other miscellaneous chlorocarbons was fed continuously to the bottoms flask so as to give a liquid residence time in the bottoms of approximately 8 hours. The feed contained no ferric chloride. Liquid draw from the reflux head was started simultaneously with the feed at a rate sufficient to maintain the liquid level in the bottoms flask. The formation rate of 1,1,2,3-tetrachloropropene, as measured by the overhead liquid composition and collection rate, peaked at 0.24 mole/hr at 8.2 hours run time, as shown in FIG. 5. The formation rate then rapidly fell to below 0.03 mole/hr at 13 hours, indicating the dehydrochlorination reaction had nearly stopped. The bottoms temperature over the course of the test steadily increased from 169-179° C.

Example 4

A feed mixture containing primarily 1,1,1,2,3-pentachloropropane was prepared by liquid-phase chlorination of 1,1,1,3-tetrachloropropane in the presence of dissolved ferric chloride. The crude chlorination product, containing approximately percent 1,1,1,2,3-pentachloropropane, 20 percent other miscellaneous chlorocarbons, and 280 ppmw ferric chloride, was charged to the bottoms flask of the distillation column. No additional solid ferric chloride was added to the liquid. The column pressure was adjusted to 350 torr, and sufficient heat was applied to the bottoms flask to reflux liquid in the column. The crude trichloropropene chlorination product containing 80 percent 1,1,1,2,3-pentachloropropane, 20 percent other miscellaneous chlorocarbons, and 280 ppmw ferric chloride was fed continuously to the bottoms flask so as to give a liquid residence time of approximately 8 hours. Liquid draw from the reflux head was started simultaneously with the feed at a rate sufficient to maintain the liquid level in the bottoms flask. Liquid was withdrawn from the bottoms flask every 2-3 hours of operation. The volume of the liquid withdrawn was about seven percent of the volume of material fed over that same time period. The formation rate of 1,1,2,3-tetrachloropropene, as measured by the overhead liquid composition and collection rate, rose to over 0.40 mole/hr by five hours run time, as shown in FIG. 5. The formation rate remained between 0.4 and 0.55 moles/hr for over 70 hours of operation, with no sign of decreasing. The bottoms temperature over the course of the test remained between 154-157° C. Ferric chloride concentration in the bottoms rose to approximately 2100 ppmw by 40 hours of operation and remained constant.

Examples 5-6 Semibatch 1,1,1,2,3-Pentachloropropane Reactions

Example 5

No Carbon Tetrachloride

A mixture of 655 ppm ferric chloride in 99+% pure 1,1,1,3-tetrachloropropane feedstock was heated and stirred in a 1-liter flask at 54-60 C for 6.22 hours, while 0.68 to 0.82 moles of chlorine per hour per kg of liquid feed was fed. Hydrogen chloride exited the reactor continuously, via a water cooled condenser, and then through a pressure control valve. Reactor pressure was kept at about 5-7 psig. Samples of liquid were taken from the reactor periodically, with the following results:

TABLE 2

| Results of Example 5 | | | | | | | |
|---|---|---|---|---|---|---|---|
| time | hr | 0.00 | 1.30 | 2.35 | 3.50 | 4.50 | 6.22 |
| sample no. | | 53202501 | 53302701 | 53302703 | 53302801 | 53302803 | 53302805 |
| weight, total, postulated | G | 817 | 820 | 835 | 815 | 845 | 909 |
| chlorine feed | mol/hr/kg | | 0.68 | 0.75 | 0.82 | 0.79 | 0.74 |
| temperature avg. | C. | | 52.9 | 54.3 | 54.7 | 57.7 | 55.9 |
| concentrations | | | | | | | |
| $FeCl_3$ | wt % | 0.065 | 0.065 | 0.064 | 0.066 | 0.063 | 0.059 |
| propene, 1,1,3-trichloro- | wt % | 0.00 | 0.14 | 2.57 | 22.14 | 14.80 | 1.09 |
| propane, 1,1,1,3-tetrachloro- | wt % | 99.93 | 86.96 | 73.93 | 21.63 | 14.32 | 8.31 |
| propene, 1,1,2,3-tetrachloro- | wt % | 0.00 | 0.05 | 0.21 | 0.46 | 0.62 | 0.93 |

TABLE 2-continued

| Results of Example 5 | | | | | | | |
|---|---|---|---|---|---|---|---|
| propane, 1,1,1,2,3-pentachloro- | wt % | 0.00 | 2.70 | 17.34 | 33.19 | 44.13 | 65.55 |
| total GC Components | wt % | 100.00 | 91.56 | 95.81 | 88.37 | 82.88 | 86.72 |
| useful product yield, on 1,1,1,3-tetrachloropropane | mol/kg | 5.49 | 4.92 | 5.05 | 4.27 | 3.88 | 3.61 |
| propane, 1,1,1,2,3-pentachloro- | % | | 2.3 | 14.9 | 27.9 | 38.4 | 61.4 |
| useful product | % | | 89.9 | 94.0 | 77.5 | 73.0 | 73.2 |

In this and the following tables, "useful product" refers to the sum of 1,1,1,2,3-pentachloropropane, 1,1,2,3-tetrachloropropene, and 1,1,3-trichloropropene. The yields are calculated on 1,1,1,3-tetrachloropropane fed. "GC" refers to Gas Chromatographic analyses of the indicated liquid samples.

An important observation on this table is that the "useful product" declined after the sample at 2.35 hour from 94% yield on 1,1,1,3-tetrachloropropane fed to 73%. Likewise, the total GC components declined from 96% at 2.35 hours to 87% at the end of 6.2 hours. The GC showed increasing amounts of components that, judging by the retention times, boil considerably higher than 1,1,1,2,3-pentachloropropane. For example, the last sample, no. 53302805, contained twenty-three components with retention times longer than 1,1,1,2,3-pentachloropropane, totaling 8.7 area % on the sample. Thus, high boilers were being produced at undesirably high rates.

Example 6

With Carbon Tetrachloride in Feed

A mixture of 51.6 wt % carbon tetrachloride and 48.3 wt % 1,1,1,3-tetrachloropropane was stirred and heated with 608 ppm ferric chloride. This experiment ran for 4.75 hours, feeding 0.59 to 0.73 moles of chlorine per hour per kg of liquid feed, keeping the temperature around 53-55 C.

In this case, total "useful product" declined from 99% yield on 1,1,1,3-tetrachloropropane fed at 2.95 hours, to 91% yield at 4.75 hours. The last sample, 53304504, contained ten components that eluted after 1,1,1,2,3-pentachloropropane on the GC, totaling 2.7 area %. The peak yield of 1,1,1,2,3-pentachloropropane was 89%, at 3.9 hours. Comparison of Example 6 with Example 5 shows an improvement in results caused by the presence of carbon tetrachloride in the feeds.

Examples 7-10 Continuous 1,1,1,2,3-Pentachloropropane Reactions

Example 7

The equipment shown in FIG. 6 was employed.

For this experiment (trial number 53315304) the feed mixture was produced in a pilot plant unit. The pilot plant unit reacted carbon tetrachloride and ethylene in a 10-gallon stirred vessel, in the presence of ferric chloride, iron metal, and tributylphosphate. The reactor effluent was distilled to separate 1,1,1,3-tetrachloropropane and lower boiling materials (the overhead fraction) from higher boiling materials, including iron and phosphorus compounds. The overhead fraction (sample number 53313710) contained 13.6 wt % carbon tetrachloride, 84.8 wt % 1,1,1,3-tetrachloropropane, 0.23 wt % chloroform, 0.08 wt % 1-chlorobutane, 0.17 wt % perchloroethylene, and 1.1 wt % other volatile materials. It was a clear colorless liquid.

TABLE 3

| Results of Example 6 | | | | | | | |
|---|---|---|---|---|---|---|---|
| Time | hr | 0.00 | 1.25 | 2.00 | 2.95 | 3.90 | 4.75 |
| sample no. | | 53303101 | 53304401 | 53304403 | 53304405 | 53304501 | 53304504 |
| weight, total, postulated | g | 893 | 903 | 914 | 938 | 965 | 965 |
| chlorine feed | mol/hr/kg | | 0.62 | 0.73 | 0.71 | 0.69 | 0.59 |
| temperature avg. | C. | | 53.3 | 54.3 | 54.6 | 54.7 | 52.9 |
| Pressure | psig | | 5.7 | 5.5 | 5.1 | 5.0 | 5.7 |
| Concentrations | | | | | | | |
| FeCl$_3$ | wt % | 0.061 | 0.060 | 0.059 | 0.058 | 0.056 | 0.056 |
| carbon tetrachloride | wt % | 51.63 | 49.82 | 48.83 | 47.01 | 44.77 | 43.69 |
| propene, 1,1,3-trichloro- | wt % | | 0.09 | 5.38 | 4.93 | 0.04 | 0.03 |
| propane, 1,1,1,3-tetrachloro- | wt % | 48.31 | 41.41 | 22.27 | 6.97 | 2.44 | 1.22 |
| propene, 1,1,2,3-tetrachloro- | wt % | | 0.10 | 0.35 | 0.66 | 0.65 | 0.07 |
| propane, 1,1,1,2,3-pentachloro- | wt % | | 7.51 | 23.35 | 37.81 | 47.35 | 47.00 |
| total GC components | wt % | 100.00 | 99.41 | 101.03 | 100.17 | 98.11 | 95.20 |
| useful product yield, on 1,1,1,3-tetrachloropropane fed | mol/kg | 2.66 | 2.63 | 2.69 | 2.51 | 2.36 | 2.25 |
| propane, 1,1,1,2,3-pentachloro- | % | | 13.2 | 41.6 | 69.1 | 89.1 | 88.4 |
| useful product | % | | 100.4 | 103.9 | 99.1 | 96.2 | 91.4 |

Some of this overhead fraction was placed in D1, shown in FIG. 6. This material was fed into the reactor, via the pump P1, at 200 grams per hour. Ferric chloride solid was periodically weighed into D2, which was made of ¼" OD polytetrafluoroethylene tubing. About 0.3 gram ferric chloride was added to the reactor every two hours of operation. The average ferric chloride concentration in the reactor liquid was 740 ppm by weight. Chlorine was fed via a 0.125" OD polytetrafluoroethylene tubing, which extended below the surface of the liquid. The chlorine to 1,1,1,3-tetrachloropropane feed ratio was 1.00 mol/mol. The reactor liquid was stirred at about 110 rpm. Reactor liquid temperature was maintained at about 77 C, and pressure was kept at 10 psig. Reactor liquid volume was about 1.05 liters, and the estimated liquid effluent flow rate was 0.155 liters per hour, so that the estimated turnover time was 6.8 hours. Chlorine and hydrogen chloride flow rates in the vent stream were measured via timed samples caught in potassium iodide solution. At the end of 15.0 hours operation (about 2.0 liquid turnovers), a sample of the liquid reactor effluent was analyzed by gas chromatography.

Chlorine conversion was 99%; 1,1,1,3-tetrachloropropane conversion was 99%. The yields of 1,1,3-trichloropropene, 1,1,1,2,3-pentachloropropane, and 1,1,2,3-tetrachloropropene on 1,1,1,3-tetrachloropropane fed were 2.0, 85, and 5.8 percent, respectively. The total yield of four prominent high-boiling byproducts was 3.3 wt % in the reactor effluent. These byproducts are believed to be hexachloropropane, two pentachlorohexene isomers, and hexachlorohexadiene.

Example 8

The feedstock (sample 53311408) for this example (trial 53313101) was produced by the same pilot plant unit as before, in the same manner. It contained 15.69 wt % carbon tetrachloride, 82.76 wt % 1,1,1,3-tetrachloropropane, 0.18 wt % chloroform, 0.03 wt % 1-chlorobutane, 0.31 wt % perchloroethylene, and 1.0 wt % other volatile materials. The experiment was performed like Example 7, except for the following changes. Reactor temperature was kept at 82 C; liquid turnover time was 7.3 hours; ferric chloride average concentration was 550 ppm; total run time was 2.1 turnovers.

Chlorine conversion was 99%; 1,1,1,3-tetrachloropropane conversion was 99%. The yields of 1,1,3-trichloropropene, 1,1,1,2,3-pentachloropropane, and 1,1,2,3-tetrachloropropene on 1,1,1,3-tetrachloropropane fed were 3.4, 82.9, and 8.1 percent, respectively. The yield of the same four undesired prominent high-boiling byproducts was 4.2 wt % in the reactor effluent.

Example 9

The starting material for this example (trial 53315701) was produced by the same pilot plant unit as before, in the same way. However, the carbon tetrachloride was then separated from the 1,1,1,3-tetrachloropropane by distillation, producing sample 53315501. The latter material contained 0.06 wt % carbon tetrachloride, 0.21 wt % 1,1,3-trichloropropene, 0.041 wt % perchloroethylene, 99.60 wt % 1,1,1,3-tetrachloropropane, and 0.09 wt % other volatile components. This material was placed in D1 and fed to the reactor. The experiment was performed like Example 8, except for the difference in the feedstock. Reactor temperature was kept at 82 C; liquid turnover time was 7.3 hours; ferric chloride average concentration was 510 ppm; total run time was 2.1 turnovers.

Chlorine conversion was 97%; 1,1,1,3-tetrachloropropane conversion was 99%. The yields of 1,1,3-trichloropropene, 1,1,1,2,3-pentachloropropane, and 1,1,2,3-tetrachloropropene on 1,1,1,3-tetrachloropropane fed were 3.7, 76.7, and 7.6 percent, respectively. The yield of the usual four undesired prominent high-boiling byproducts was 6.3 wt % in the reactor effluent. Comparison of this experiment with Example 8 shows a significant advantage for the feedstock containing 15.7 wt % carbon tetrachloride.

Example 10

The liquid feedstock (sample 53315312) for this example (trial 53317907) was produced by the same pilot plant unit as in Example 7. It contained 22.46 wt % carbon tetrachloride, 76.09 wt % 1,1,1,3-tetrachloropropane, 0.23 wt % chloroform, 0.09 wt % 1-chlorobutane, 0.13 wt % perchloroethylene, and 1.0 wt % other volatile materials. The experiment was conducted at higher temperature, with less ferric chloride catalyst, relative to Example 7. Reactor temperature was kept at 92 C; liquid turnover time was 7.2 hours; ferric chloride average concentration was 180 ppm; total run time was 2.0 turnovers. Reactor pressure was 9-10 psig, as usual.

Chlorine conversion was 98%; 1,1,1,3-tetrachloropropane conversion was 97%. The yields of 1,1,3-trichloropropene, 1,1,1,2,3-pentachloropropane, and 1,1,2,3-tetrachloropropene on 1,1,1,3-tetrachloropropane fed were 2.7, 85, and 5.7 percent, respectively. The yield of the usual four undesired prominent high-boiling byproducts was 2.2 wt % in the reactor effluent.

All references cited herein are hereby incorporated by reference in their entireties. A number of embodiments of the invention have been described. Nevertheless, it will be understood that various modifications may be made without departing from the spirit and scope of the invention. Accordingly, other embodiments are within the scope of the following claims.

What is claimed is:

1. A process for the substantially continuous production of 1,1,1,2,3-pentachloropropane, the process comprising:
   (i) substantially continuously feeding 1,1,1,3-tetrachloropropane to a reactor;
   (ii) substantially continuously feeding chlorine to the reactor, wherein the chlorine is provided by a chlorine feedstock that is substantially pure and dry;
   (iii) substantially continuously feeding ferric chloride to the reactor;
   (iv) maintaining the reactor at conditions of temperature and pressure sufficient to produce 1,1,1,2,3-pentachloropropane within the reactor; and
   (v) substantially continuously removing 1,1,1,2,3-pentachloropropane from the reactor.

2. The process of claim 1, further comprising the step of substantially continuously removing hydrogen chloride from the reactor.

3. The process of claim 1, where the chlorine/1,1,1,3-tetrachloropropane feed ratio is carefully controlled as to not form excessive amounts of compounds containing six carbon atoms and as to not form excessive amounts of over chlorinated materials.

4. The process of claim 1, where said step of substantially continuously feeding ferric chloride maintains a ferric chloride concentration within the reactor in a catalytic amount.

5. The process of claim 1, wherein the chlorine feedstock includes less than about 0.5 wt % water.

6. A process for the manufacture of 1,1,2,3-tetrachloropropene, the process comprising:
  (i) reacting 1,1,1,3-tetrachloropropane with chlorine in the presence of ferric chloride and carbon tetrachloride to produce crude 1,1,1,2,3-pentachloropropane, where the carbon tetrachloride is present in an amount of from 3 to 30 wt %, where the ratio of chlorine to 1,1,1,3-tetrachloropropane is carefully controlled to achieve the desired reaction between 1,1,1,3-tetrachloropropane and chlorine;
  (ii) feeding the crude 1,1,1,2,3-pentachloropropane into a reaction zone, to transform the crude 1,1,1,2,3-pentachloropropane into 1,1,2,3-tetrachloropropene and hydrogen chloride by dehydrochlorination, where the reaction zone is maintained at a temperature such that at least a portion of the 1,1,2,3-tetrachloropropene and hydrogen chloride move from the reaction zone during the course of the dehydrochlorination reaction to a separation zone; and
  (iii) collecting 1,1,2,3-tetrachloropropene.

7. The process of claim 6, wherein from about 1000 to about 20000 ppm by weight of ferric chloride is maintained in the reaction zone.

8. A process for the manufacture of 1,1,2,3-tetrachloropropene, the process comprising dehydrochlorinating 1,1,1,2,3-pentachloropropane to thereby produce 1,1,2,3-tetrachloropropene at a formation rate, as measured by an overhead liquid composition rate, of at least 0.40 mole/hour after five hours of operation run time.

9. The process of claim 8, wherein the formation rate of 1,1,2,3-tetrachloropropene remains between 0.40 and 0.55 mole/hour for at least 70 hours of operation run time.

* * * * *